US012649781B2

(12) United States Patent
Gekkieva et al.

(10) Patent No.: US 12,649,781 B2
(45) Date of Patent: Jun. 9, 2026

(54) METHODS FOR TREATING DIABETIC RETINOPATHY USING BROLUCIZUMAB

(71) Applicant: NOVARTIS AG, Basel (CH)

(72) Inventors: Margarita Gekkieva, Basel (CH); Philippe Maria Clotaire Margaron, Reinach (CH)

(73) Assignee: Novartis AG, Basel (CH)

( * ) Notice: Subject to any disclaimer, the term of this patent is extended or adjusted under 35 U.S.C. 154(b) by 1045 days.

(21) Appl. No.: 17/641,799

(22) PCT Filed: Sep. 11, 2020

(86) PCT No.: PCT/IB2020/058459
§ 371 (c)(1),
(2) Date: Mar. 9, 2022

(87) PCT Pub. No.: WO2021/048806
PCT Pub. Date: Mar. 18, 2021

(65) Prior Publication Data
US 2024/0052024 A1 Feb. 15, 2024

Related U.S. Application Data

(60) Provisional application No. 62/971,405, filed on Feb. 7, 2020, provisional application No. 62/899,892, filed on Sep. 13, 2019.

(51) Int. Cl.
| | |
|---|---|
| *A61K 39/395* | (2006.01) |
| *A61P 27/02* | (2006.01) |
| *C07K 16/22* | (2006.01) |
| *A61K 39/00* | (2006.01) |

(52) U.S. Cl.
CPC ............. *C07K 16/22* (2013.01); *A61P 27/02* (2018.01); *A61K 2039/505* (2013.01); *A61K 2039/54* (2013.01); *A61K 2039/545* (2013.01); *C07K 2317/24* (2013.01); *C07K 2317/622* (2013.01); *C07K 2317/76* (2013.01)

(58) Field of Classification Search
None
See application file for complete search history.

(56) References Cited

U.S. PATENT DOCUMENTS

| | | | |
|---|---|---|---|
| 8,293,235 | B2 | 10/2012 | Borras et al. |
| 8,349,322 | B2 | 1/2013 | Borras et al. |
| 8,673,310 | B2 | 3/2014 | Borras et al. |
| 8,937,162 | B2 | 1/2015 | Borras et al. |
| 9,090,684 | B2 | 7/2015 | Borras et al. |
| 9,422,366 | B2 | 8/2016 | Borras et al. |
| 9,593,161 | B2 | 3/2017 | Borras et al. |
| 9,873,737 | B2 | 1/2018 | Borras et al. |
| 10,035,850 | B2 | 7/2018 | Gekkieva et al. |
| 10,087,244 | B2 | 10/2018 | Borras et al. |
| 10,100,111 | B2 | 10/2018 | Borras et al. |
| 10,590,193 | B2 | 3/2020 | Borras et al. |
| 10,689,438 | B2 | 6/2020 | Zhang et al. |
| 11,098,110 | B2 | 8/2021 | Gekkieva et al. |
| 2016/0220675 | A1 | 8/2016 | Abrahmsohn |
| 2018/0127493 | A1 | 5/2018 | Borras et al. |
| 2018/0251545 | A1 | 9/2018 | Cao et al. |
| 2018/0371074 | A1 | 12/2018 | Borras et al. |
| 2020/0172608 | A1 | 6/2020 | Borras et al. |
| 2020/0190179 | A1 | 6/2020 | Sigg et al. |
| 2020/0270336 | A1 | 8/2020 | Zhang et al. |
| 2021/0017266 | A1 | 1/2021 | Racine et al. |
| 2021/0340242 | A1 | 11/2021 | Gekkieva et al. |

FOREIGN PATENT DOCUMENTS

| | | |
|---|---|---|
| EP | 2451438 B1 | 2/2014 |
| RU | 2696972 C1 | 8/2019 |
| WO | 2016073915 A1 | 5/2016 |
| WO | 2016073918 A1 | 5/2016 |
| WO | 2017194779 A1 | 11/2017 |
| WO | WO-2021/048806 A1 | 3/2021 |

OTHER PUBLICATIONS

DrugBank.com ID DB14864, Brolucizumab, Retrieved online from: <URL:https://go.drugbank.com/drugs/DB14864> [retrieved on Aug. 28, 2025], 7 pages, Sep. 6, 2024.*

Jin et al., Ocular delivery systems for the administration of antibody therapeutics, J. Pharma. Invest. 47:373-382, 2017.*

PA Health & Wellness, Clinical Policy: Ranibizumab (Lucentis), Retrieved from: <UR:https://www.pahealthwellness.com > dam > policies> [retrieved on Aug. 28, 2025], 6 pages, Jan. 2019.*

Sun et al., Rationale and Application of the Protocol S Anti-Vascular Endothelial Growth Factor Algorithm for Proliferative Diabetic Retinopathy, Ophthalmol. 126:87-95, 2019.*

Joseph A. Intravitreal injections: A brief note. Kerala J, Ophthalmol. 30:63-66, 2018.*

Dugel et al., Hawk and Harrier: Phase 3, Multicenter, Randomized, Double-Masked Trials of Brolucizumab for Neovascular Age-Related Macular Degeneration, Ophthalmology, Apr. 12, 2019, pp. 72-84, vol. 127, No. 1.

Yannuzzi et al., Brolucizumab: evidence to date in the treatment of neovascular age-related macular degeneration, Clinical Ophthalmology, Jul. 24, 2019, 1323-1329, vol. 13.

Singh et al., Advances in the treatment of Diabetic Retinopathy, Journal of Diabetes and its Complications, Aug. 15, 2019, 1-9, vol. 33 No. 12, Elsevier Science, New York, US.

Gonzalez, The Impact on Vision and Regression of Retinal Neovascularization of Anti-VEGF Induction in Combination with Quarterly Anti-VEGF Maintenance or Selective PRP versus Standard PRP, Investigative Ophthalmology & Visual Science ARVO Meeting Abstract, Jun. 1, 2013.

Zhao et al., The role of anti-vascular endothelial growth factor (anti-VEGF) in the management of proliferative diabetic retinopathy, Drugs in Context, Aug. 13, 2018, 1-10, vol. 7.

(Continued)

*Primary Examiner* — Claire Kaufman
(74) *Attorney, Agent, or Firm* — Foley Hoag LLP; Brendan T. Jones; Morgan Xu

(57) ABSTRACT

A method is provided for treating a patient having a neovascular ocular disease.

24 Claims, No Drawings
Specification includes a Sequence Listing.

(56)           References Cited

OTHER PUBLICATIONS

Clinical Trial NCT05112835, Nov. 9, 2021, available at https://www.clinicaltrials.gov/ct2/show/NCT05112835.

Sacconi, et al., Emerging therapies in the management of macular edema: a review, F1000Research, 8(1413), 1-10, 2019.

U.S. Appl. No. 17/916,980.

Bates, et al., David vs. Goliath: The Structure, Function, and Clinical Prospects of Antibody Fragments, Antibodies, 8(28), 1-31, 2019.

Cooper, At Al., Role of heavy chain constant domains in antibody-antigen interaction. Apparent specificity differences among streptococcal IgG antibodies expressing identical variable domains, J Immunol., 150, 2231-2242, 1993.

Kazaykin, Diabetic retinopathy: clinical picture, diagnostics and treatment, 1-35, 2016.

Liang, et al., Dramatic activation of an antibody by a single amino acid change in framework, Scientific Reports, 11, 22365, 2021.

International Search Report and Written Opinion for International Application No. PCT/IB20/58459 dated Jan. 21, 2021.

Kim et al., "Efficacy and Safety of Brolucizumab in Proliferative Diabetic Retinopathy: 2-Year Results from the CONDOR Study" Investigative Ophthalmology & Visual Science, vol. 66, p. 4759 (2025).

* cited by examiner

SEQUENCE LISTING

<160> NUMBER OF SEQ ID NOS: 10

<210> SEQ ID NO 1
<211> LENGTH: 120
<212> TYPE: PRT
<213> ORGANISM: Artificial Sequence
<220> FEATURE:
<223> OTHER INFORMATION: Synthetic heavy chain variable domain

<400> SEQUENCE: 1

```
Glu Val Gln Leu Val Glu Ser Gly Gly Gly Leu Val Gln Pro Gly Gly
1               5                   10                  15

Ser Leu Arg Leu Ser Cys Thr Ala Ser Gly Phe Ser Leu Thr Asp Tyr
            20                  25                  30

Tyr Tyr Met Thr Trp Val Arg Gln Ala Pro Gly Lys Gly Leu Glu Trp
        35                  40                  45

Val Gly Phe Ile Asp Pro Asp Asp Pro Tyr Tyr Ala Thr Trp Ala
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Gly Gly Asp His Asn Ser Gly Trp Gly Leu Asp Ile Trp Gly Gln
            100                 105                 110

Gly Thr Leu Val Thr Val Ser Ser
            115                 120
```

<210> SEQ ID NO 2
<211> LENGTH: 111
<212> TYPE: PRT
<213> ORGANISM: Artificial Sequence
<220> FEATURE:
<223> OTHER INFORMATION: Synthetic light chain variable domain

<400> SEQUENCE: 2

```
Glu Ile Val Met Thr Gln Ser Pro Ser Thr Leu Ser Ala Ser Val Gly
1               5                   10                  15

Asp Arg Val Ile Ile Thr Cys Gln Ala Ser Glu Ile Ile His Ser Trp
            20                  25                  30

Leu Ala Trp Tyr Gln Gln Lys Pro Gly Lys Ala Pro Lys Leu Leu Ile
        35                  40                  45

Tyr Leu Ala Ser Thr Leu Ala Ser Gly Val Pro Ser Arg Phe Ser Gly
    50                  55                  60

Ser Gly Ser Gly Ala Glu Phe Thr Leu Thr Ile Ser Ser Leu Gln Pro
65                  70                  75                  80

Asp Asp Phe Ala Thr Tyr Tyr Cys Gln Asn Val Tyr Leu Ala Ser Thr
                85                  90                  95

Asn Gly Ala Asn Phe Gly Gln Gly Thr Lys Leu Thr Val Leu Gly
            100                 105                 110
```

<210> SEQ ID NO 3
<211> LENGTH: 251
<212> TYPE: PRT
<213> ORGANISM: Artificial Sequence
<220> FEATURE:
<223> OTHER INFORMATION: Synthetic single-chain antibody

<400> SEQUENCE: 3

```
Glu Ile Val Met Thr Gln Ser Pro Ser Thr Leu Ser Ala Ser Val Gly
1               5                   10                  15

Asp Arg Val Ile Ile Thr Cys Gln Ala Ser Glu Ile Ile His Ser Trp
            20                  25                  30

Leu Ala Trp Tyr Gln Gln Lys Pro Gly Lys Ala Pro Lys Leu Leu Ile
        35                  40                  45

Tyr Leu Ala Ser Thr Leu Ala Ser Gly Val Pro Ser Arg Phe Ser Gly
    50                  55                  60

Ser Gly Ser Gly Ala Glu Phe Thr Leu Thr Ile Ser Ser Leu Gln Pro
65                  70                  75                  80

Asp Asp Phe Ala Thr Tyr Tyr Cys Gln Asn Val Tyr Leu Ala Ser Thr
                85                  90                  95

Asn Gly Ala Asn Phe Gly Gln Gly Thr Lys Leu Thr Val Leu Gly Gly
            100                 105                 110

Gly Gly Gly Ser Gly Gly Gly Gly Ser Gly Gly Gly Gly Ser Gly Gly
        115                 120                 125

Gly Gly Ser Glu Val Gln Leu Val Glu Ser Gly Gly Gly Leu Val Gln
    130                 135                 140

Pro Gly Gly Ser Leu Arg Leu Ser Cys Thr Ala Ser Gly Phe Ser Leu
145                 150                 155                 160

Thr Asp Tyr Tyr Tyr Met Thr Trp Val Arg Gln Ala Pro Gly Lys Gly
                165                 170                 175

Leu Glu Trp Val Gly Phe Ile Asp Pro Asp Asp Pro Tyr Tyr Ala
            180                 185                 190

Thr Trp Ala Lys Gly Arg Phe Thr Ile Ser Arg Asp Asn Ser Lys Asn
```

-continued

```
            195                 200                 205

Thr Leu Tyr Leu Gln Met Asn Ser Leu Arg Ala Glu Asp Thr Ala Val
    210                 215                 220

Tyr Tyr Cys Ala Gly Gly Asp His Asn Ser Gly Trp Gly Leu Asp Ile
225                 230                 235                 240

Trp Gly Gln Gly Thr Leu Val Thr Val Ser Ser
                245                 250

<210> SEQ ID NO 4
<211> LENGTH: 252
<212> TYPE: PRT
<213> ORGANISM: Artificial Sequence
<220> FEATURE:
<223> OTHER INFORMATION: Synthetic single-chain antibody

<400> SEQUENCE: 4

Met Glu Ile Val Met Thr Gln Ser Pro Ser Thr Leu Ser Ala Ser Val
1               5                   10                  15

Gly Asp Arg Val Ile Ile Thr Cys Gln Ala Ser Glu Ile Ile His Ser
            20                  25                  30

Trp Leu Ala Trp Tyr Gln Gln Lys Pro Gly Lys Ala Pro Lys Leu Leu
        35                  40                  45

Ile Tyr Leu Ala Ser Thr Leu Ala Ser Gly Val Pro Ser Arg Phe Ser
    50                  55                  60

Gly Ser Gly Ser Gly Ala Glu Phe Thr Leu Thr Ile Ser Ser Leu Gln
65                  70                  75                  80

Pro Asp Asp Phe Ala Thr Tyr Tyr Cys Gln Asn Val Tyr Leu Ala Ser
                85                  90                  95

Thr Asn Gly Ala Asn Phe Gly Gln Gly Thr Lys Leu Thr Val Leu Gly
            100                 105                 110

Gly Gly Gly Gly Ser Gly Gly Gly Gly Ser Gly Gly Gly Gly Ser Gly
        115                 120                 125

Gly Gly Gly Ser Glu Val Gln Leu Val Glu Ser Gly Gly Gly Leu Val
    130                 135                 140

Gln Pro Gly Gly Ser Leu Arg Leu Ser Cys Thr Ala Ser Gly Phe Ser
145                 150                 155                 160

Leu Thr Asp Tyr Tyr Tyr Met Thr Trp Val Arg Gln Ala Pro Gly Lys
                165                 170                 175

Gly Leu Glu Trp Val Gly Phe Ile Asp Pro Asp Asp Asp Pro Tyr Tyr
            180                 185                 190

Ala Thr Trp Ala Lys Gly Arg Phe Thr Ile Ser Arg Asp Asn Ser Lys
        195                 200                 205

Asn Thr Leu Tyr Leu Gln Met Asn Ser Leu Arg Ala Glu Asp Thr Ala
    210                 215                 220

Val Tyr Tyr Cys Ala Gly Gly Asp His Asn Ser Gly Trp Gly Leu Asp
225                 230                 235                 240

Ile Trp Gly Gln Gly Thr Leu Val Thr Val Ser Ser
                245                 250

<210> SEQ ID NO 5
<211> LENGTH: 11
<212> TYPE: PRT
<213> ORGANISM: Artificial Sequence
<220> FEATURE:
<223> OTHER INFORMATION: CDRL1

<400> SEQUENCE: 5
```

-continued

```
Gln Ala Ser Glu Ile Ile His Ser Trp Leu Ala
1               5                   10

<210> SEQ ID NO 6
<211> LENGTH: 7
<212> TYPE: PRT
<213> ORGANISM: Artificial Sequence
<220> FEATURE:
<223> OTHER INFORMATION: CDRL2

<400> SEQUENCE: 6

Leu Ala Ser Thr Leu Ala Ser
1               5

<210> SEQ ID NO 7
<211> LENGTH: 12
<212> TYPE: PRT
<213> ORGANISM: Artificial Sequence
<220> FEATURE:
<223> OTHER INFORMATION: CDRL3

<400> SEQUENCE: 7

Gln Asn Val Tyr Leu Ala Ser Thr Asn Gly Ala Asn
1               5                   10

<210> SEQ ID NO 8
<211> LENGTH: 11
<212> TYPE: PRT
<213> ORGANISM: Artificial Sequence
<220> FEATURE:
<223> OTHER INFORMATION: CDRH1

<400> SEQUENCE: 8

Gly Phe Ser Leu Thr Asp Tyr Tyr Tyr Met Thr
1               5                   10

<210> SEQ ID NO 9
<211> LENGTH: 16
<212> TYPE: PRT
<213> ORGANISM: Artificial Sequence
<220> FEATURE:
<223> OTHER INFORMATION: CDRH2

<400> SEQUENCE: 9

Phe Ile Asp Pro Asp Asp Asp Pro Tyr Tyr Ala Thr Trp Ala Lys Gly
1               5                   10                  15

<210> SEQ ID NO 10
<211> LENGTH: 11
<212> TYPE: PRT
<213> ORGANISM: Artificial Sequence
<220> FEATURE:
<223> OTHER INFORMATION: CDRH3

<400> SEQUENCE: 10

Gly Asp His Asn Ser Gly Trp Gly Leu Asp Ile
1               5                   10
```

METHODS FOR TREATING DIABETIC RETINOPATHY USING BROLUCIZUMAB

This application is a U.S. National Phase filing of International Application Serial No. PCT/IB2020/058459 filed 11 Sep. 2020, which claims the benefit of priority to U.S. Provisional Application No. 62/899,892 filed 13 Sep. 2019 and U.S. Provisional Application No. 62/971,405 filed 7 Feb. 2020, the disclosures of each of which is incorporated herein by reference in their entireties.

SEQUENCE LISTING

The instant application contains a Sequence Listing which has been submitted electronically in ASCII format and is hereby incorporated in its entirety. Said ASCII copy, created on Jul. 28, 2020, is named PAT058689_SEQ_LISTING_ST25.txt and is 8282 bytes in size.

FIELD OF THE INVENTION

The invention relates to methods for treating ocular disease with a VEGF antagonist. In particular, the invention relates to treating neovascular ocular disease, such as diabetic retinopathy and proliferative diabetic retinopathy, with less frequent dosing than currently approved treatment regimens.

BACKGROUND OF THE INVENTION

Diabetes mellitus (DM) is the most common endocrine disease in developed countries, with prevalence estimates ranging between 2 to 5% of the world population. Diabetic retinopathy (DR) and diabetic macular edema (DME) are common microvascular complications in patients with diabetes and may have a debilitating impact on visual acuity (VA), eventually leading to blindness.

DR is the most common cause of vision loss among people with diabetes and the leading cause of vision impairment and blindness in working aged adults. DR occurs when high blood glucose levels cause damage to blood vessels in the retina. These blood vessels can swell and leak or they can close, stopping blood from passing through. Sometimes abnormal new blood vessels can also grow on the retina. Diabetic retinopathy includes both non-proliferative diabetic retinopathy (nPDR) and proliferative diabetic retinopathy (PDR), the more advanced form of the disease. DME is a frequent manifestation of DR (Riordan-Eva, 2004, Eye (Lond). 2004, 18:1161-8) and is the major cause of visual loss in patients with DR. While diabetic macular edema (DME) may occur at any stage of DR, it is more likely to manifest following severe nPDR and PDR.

Currently, care providers actively monitor mild to moderate nPDR and reserve treatment for severe nPDR and PDR. Both LUCENTIS® and EYLEA® have recently gained approval for DR in the United States. For treating DR, the recommended dose of EYLEA® is 2 mg (0.05 mL) administered every 4 weeks for 5 injections followed by an injection once every 8 weeks. For treating DR, the recommended dose of LUCENTIS® is 0.3 mg (0.05 mL) administered once a month. Even though two drugs are approved for treating DR, the current standard of care is panretinal photocoagulation (PRP), a laser. Despite such treatment options, there remains a need for a treatment that reduces the injection frequency, provides better anatomical responses, and avoids invasive laser therapy.

SUMMARY

The invention provides a method of administering a therapeutic VEGF antagonist for treating proliferative diabetic retinopathy (PDR). In certain aspects, the invention provides methods for treating PDR comprising administering to a mammal at least two individual doses of a VEGF antagonist at 6-week intervals (q6w) in a loading phase, followed by additional doses in a maintenance phase, wherein at least 6 weeks separate the doses administered in the maintenance phase. In certain aspects, doses in the maintenance phase are administered no less than once every 12 weeks (q12w). In certain aspects, the dosing frequency is adjusted based on the outcome of disease activity assessments, for example using pre-defined visual and anatomic criteria. In one aspect, at any time during the maintenance phase (e.g. after Week 48 measured from the first treatment dose), the treatment interval may be extended by 6 weeks at a time up to 24 weeks, at the treatment provider's discretion based on an assessment of diabetic activity. In another aspect, dosing frequency in the maintenance phase can be adjusted by decreasing the dosing interval from once every 12 weeks (q12w) to once every 6 weeks (q6w) if disease activity is detected at any scheduled treatment visit.

The invention also provides a VEGF antagonist for use in a method of treating ocular diseases, particularly ocular neovascular diseases, more particularly diabetic retinopathy (DR) and proliferative diabetic retinopathy (PDR), in a patient, wherein the VEGF antagonist is first provided in a loading phase, during which the patient receives three individual doses of the VEGF antagonist at 6-week intervals, and then the VEGF antagonist is provided in a maintenance phase, during which the patient receives an additional dose of the VEGF antagonist once every 12 weeks (q12w). In one aspect, dosing frequency can be extended by increasing the dosing interval 6 weeks at a time to once every 24 weeks (q24w) if disease activity is not detected at a scheduled treatment visit. In another aspect, dosing frequency can be adjusted by decreasing the dosing interval from once every 12 weeks (q12w) to once every 6 weeks (q6w) if disease activity is detected at scheduled treatment visits.

The invention also provides methods for treating DR comprising administering to a mammal at least two individual doses of a VEGF antagonist at 6-week intervals (q6w) in a loading phase, followed by additional doses in a maintenance phase, wherein at least 6 weeks separate the doses administered in the maintenance phase. In certain aspects, doses in the maintenance phase are administered no less than once every 12 weeks (q12w). In certain aspects, the dosing frequency is adjusted based on the outcome of disease activity assessments, for example using pre-defined visual and anatomic criteria. In one aspect, at any time during the maintenance phase (e.g. after Week 48 measured from the first treatment dose), the treatment interval may be extended by 6 weeks at a time up to 24 weeks, at the treatment provider's discretion based on an assessment of diabetic activity. In another aspect, dosing frequency in the maintenance phase can be adjusted by decreasing the dosing interval from once every 12 weeks (q12w) to once every 6 weeks (q6w) if disease activity is detected at any scheduled treatment visit. In another aspect the patient also has macular edema (e.g., diabetic macular edema).

The invention further provides methods for preventing progression of proliferative diabetic retinopathy (PDR) to non-proliferative diabetic retinopathy (NPDR) in a patient, comprising administering to a mammal at least two individual doses of a VEGF antagonist at 6-week intervals (q6w) in a loading phase, followed by additional doses in a maintenance phase, wherein at least 6 weeks separate the doses administered in the maintenance phase. In certain aspects, doses in the maintenance phase are administered no less than once every 12 weeks (q12w). In certain aspects, the dosing frequency is adjusted based on the outcome of disease activity assessments, for example using pre-defined visual and anatomic criteria. In one aspect, at any time during the maintenance phase (e.g. after Week 48 measured from the first treatment dose), the treatment interval may be extended by 6 weeks at a time up to 24 weeks, at the treatment provider's discretion based on an assessment of diabetic activity. In another aspect, dosing frequency in the maintenance phase can be adjusted by decreasing the dosing interval from once every 12 weeks (q12w) to once every 6 weeks (q6w) if disease activity is detected at any scheduled treatment visit. In certain aspects, the patient is initially treated for NPDR. In other aspects, the patient is initially treated for DR.

The invention also provides a kit, comprising: a drug container comprising a VEGF antagonist, and instructions for using the VEGF antagonist for treating a patient diagnosed with DR, NPDR, or PDR, three doses of the VEGF antagonist administered at 6-week intervals (q6w), the last of which is followed by additional individual doses of the VEGF antagonist at 12-week intervals (q12w). In one aspect, the kit comprises one or more 6 mg doses of brolucizumab, each dose provided in a single use vial containing sufficient brolucizumab to deliver a 6 mg dose when administering a volume of 0.05 mL or in a prefilled syringe containing 6 mg of brolucizumab. In another aspect, the instructions further indicate the q12w dosing interval be adjusted to once every 6 weeks if PDR disease activity is observed in the treated eye. In another aspect, the instructions further indicate the q12w dosing interval be extended to once every 24 weeks, if no PDR disease activity is observed in the treated eye. In still another aspect, the instructions further indicate the VEGF antagonist is administered on an as needed basis, i.e., pro re nata (PRN), at the discretion of a treatment provider (e.g., a physician or other qualified medical professional) based on visual and/or anatomical outcomes to determine disease activity before or after any q12w dose.

In certain aspects, the VEGF antagonist used in a method of the invention is an anti-VEGF antibody. In a particular aspect, the anti-VEGF antibody is a single chain antibody (scFv) or Fab fragment. In particular, the anti-VEGF antibody is brolucizumab.

Non-limiting embodiments of the present disclosure are described in the following embodiments:

1. A method for treating proliferative diabetic retinopathy (PDR) in a patient, the method comprising:
  a) administering to the patient three individual doses of a VEGF antagonist at 6-week intervals; and
  b) administering to the patient one or more additional doses of the VEGF antagonist once every 12 weeks (q12w regimen), wherein the first additional dose is administered 12 weeks after the third individual dose of step a).
2. The method of embodiment 1, further comprising assessing the patient for PDR disease activity before or after administering every q12w dose.
3. The method of embodiment 2, wherein disease activity is assessed based on identifying best corrected visual acuity (BCVA), ETDRS DRSS score, retinal neovascularization status, and peripheral visual field.
4. The method of embodiment 2 or 3, wherein if worsening of PDR disease activity is identified after a q12w dose, the patient is switched to a q6w regimen, wherein the additional doses are administered once every 6 weeks instead of once every 12 weeks.
5. The method of embodiment 4, wherein the worsening of PDR disease activity is new or worsening retinal neovascularization, reperfusion of retinal neovascularization, increase in ETDRS DRSS score, loss in peripheral visual field, and/or developing complications that impact visual acuity compared to any previous assessment.
6. The method of embodiment 2 or 3, wherein at any time during the q12w treatment interval, is extended to 18 weeks (q18w) or 24 weeks (q24w) if disease activity is stable or improved relative to a prior disease activity assessment.
7. The method of any one of embodiments 1-6, wherein the patient is a human.
8. The method of any one of embodiments 1-7, wherein the anti-VEGF antagonist is brolucizumab.
9. The method of any one of embodiments 1-8, wherein the VEGF antagonist is administered by intravitreal injection.
10. The method of any one of embodiments 1-9, wherein the dosage of the VEGF antagonist is 3 mg or 6 mg.
11. A method for treating diabetic retinopathy (DR) or proliferative diabetic retinopathy (PDR) comprising administering to a patient three individual doses at 6-week intervals in a loading phase, followed by additional doses every 12 weeks (q12w regimen) in a maintenance phase, of about 3 mg or about 6 mg of a VEGF antagonist that is an anti-VEGF antibody, optionally a DR patient also has macular edema (such as diabetic macular edema).
12. The method of embodiment 11, further comprising assessing the patient's DR or PDR disease activity before or after administering every q12w dose.
13. The method of embodiment 12, wherein disease activity is assessed based on identifying best corrected visual acuity (BCVA), ETDRS DRSS score, retinal neovascularization status, and peripheral visual field.
14. The method of embodiment 12 or 13, wherein at any time during the maintenance phase the dosing intervals are extended to 24 weeks (q24w) if disease activity is improved or stable relative to the prior disease activity assessment.
15. The method of embodiment 11 to 13, wherein if worsening of PDR disease activity is identified after a q12w dose, the patient is switched to a q6w regimen, wherein the additional doses are administered once every 6 weeks instead of once every 12 weeks.
16. The method of embodiment 15, wherein the worsening of PDR disease activity is new or worsening retinal neovascularization, reperfusion of retinal neovascularization, increase in ETDRS DRSS score, loss in peripheral visual field, and/or developing complications that impact visual acuity compared to any previous assessment.
17. The method of any one of embodiments 11-16, wherein the patient is a human.
18. The method of any one of embodiments 11-17, wherein the anti-VEGF antagonist is brolucizumab.

19. The method of any one of embodiments 11-18, wherein the VEGF antagonist is administered by intravitreal injection.

20. A VEGF antagonist for use in a method of treating diabetic retinopathy (DR) or proliferative diabetic retinopathy (PDR) in a patient, wherein the VEGF antagonist is administered to the patient:
   a) in three individual doses at 6-week intervals; and
   b) as an additional dose once every 12 weeks (q12w regimen) thereafter.

21. The VEGF antagonist for use according to embodiment 20, wherein the method further comprises assessing the patient for DR or PDR disease activity before or after administering every q12w dose.

22. The VEGF antagonist for use according to embodiment 21, wherein disease activity is assessed based on identifying best corrected visual acuity (BCVA), ETDRS DRSS score, retinal neovascularization status, and peripheral visual field.

23. The VEGF antagonist for use according to embodiment 21 or 22, wherein if worsening of disease activity is identified after a q12w dose, the patient is switched to a q6w regimen, wherein the additional doses are administered once every 6 weeks instead of once every 12 weeks.

24. The VEGF antagonist for use according to embodiment 23, wherein the worsening of disease activity is new or worsening retinal neovascularization, reperfusion of retinal neovascularization, increase in ETDRS DRSS score (such as an increase of 2 or more steps), loss in peripheral visual field, and/or developing complications that impact visual acuity compared to any previous assessment.

25. The VEGF antagonist for use according to any one of embodiments 20 to 22, wherein at any time during the maintenance phase the dosing intervals are extended to 24 weeks (q24w) if disease activity is improved or stable relative to the prior disease activity assessment.

26. The VEGF antagonist for use according to any one of embodiments 20-25, wherein the patient is a human.

27. The VEGF antagonist for use according to any one of embodiments 20-26, wherein the anti-VEGF antagonist is brolucizumab.

28. The VEGF antagonist for use according to any one of embodiments 20-27, wherein the VEGF antagonist is administered by intravitreal injection.

29. The VEGF antagonist for use according to any one of embodiments 20-28, wherein the dose of the VEGF antagonist is about 3 mg to about 6 mg.

30. A VEGF antagonist for use in a method of treating diabetic retinopathy (DR) or proliferative diabetic retinopathy (PDR) in a patient, wherein the VEGF antagonist is first provided in a loading phase, during which the patient receives three individual doses of about 3 mg or about 6 mg of the VEGF antagonist at 6-week intervals, and then the VEGF antagonist is provided in a maintenance phase, during which the patient receives an additional about 3 mg or about 6 mg dose of the VEGF antagonist once every 12 weeks (q12w regimen).

31. The VEGF antagonist for use according to embodiment 30, wherein the method further comprises assessing the patient for DR or PDR disease activity before or after administering every q12w dose.

32. The VEGF antagonist for use according to embodiment 31, wherein disease activity is assessed based on identifying best corrected visual acuity (BCVA), ETDRS DRSS score, retinal neovascularization status, and peripheral visual field.

33. The VEGF antagonist for use according to embodiment 31 or 32, wherein if worsening of disease activity is new or worsening retinal neovascularization, reperfusion of retinal neovascularization, increase in ETDRS DRSS score (such as an increase of 2 or more steps), loss in peripheral visual field, and/or developing complications that impact visual acuity compared to any previous assessment.

34. The VEGF antagonist for use according to embodiment 33, wherein the worsening of PDR disease activity is new or worsening retinal neovascularization, reperfusion of retinal neovascularization, increase in ETDRS DRSS score, loss in peripheral visual field, and/or developing complications that impact visual acuity compared to any previous assessment.

35. The VEGF antagonist for use according to any one of embodiments 30 to 32, wherein at any time during the maintenance phase the dosing intervals are extended to 24 weeks (q24w) if disease activity is improved or stable relative to the prior disease activity assessment.

36. The VEGF antagonist for use according to any one of embodiments 30-35, wherein the patient is a human.

37. The VEGF antagonist for use according to any one of embodiments 30-36, wherein the anti-VEGF antagonist is brolucizumab.

38. The VEGF antagonist for use according to any one of embodiments 30-37, wherein the VEGF antagonist is administered by intravitreal injection.

39. A kit, comprising:
   a) a drug container comprising a VEGF antagonist, and
   b) instructions for using the VEGF antagonist for treating a patient diagnosed with DR or PDR, three doses of the VEGF antagonist administered at 6-week intervals (q6w), the last of which is followed by additional individual doses of the VEGF antagonist at 12-week intervals (q12w).

40. The kit of embodiment 39, comprising
   (a) one or more 6 mg doses of brolucizumab, each dose provided in a single use vial containing sufficient brolucizumab to deliver a 6 mg dose when administering a volume of 0.05 mL or in a prefilled syringe containing 6 mg of brolucizumab, or
   (b) one or more 3 mg doses of brolucizumab, each dose provided in a single use vial containing sufficient brolucizumab to deliver a 3 mg dose when administering a volume of 0.05 mL or in a prefilled syringe containing 3 mg of brolucizumab.

41. The kit of embodiment 39 or 40, wherein the instructions further indicate the q12w dosing interval be adjusted to once every 6 weeks if DR or PDR disease activity is observed in the treated eye.

42. The kit of embodiment 39 or 40, wherein the instructions further indicate the q12w dosing interval be extended to once every 24 weeks, 6 weeks at a time, if no disease activity is observed in the treated eye.

43. The kit of embodiment 39 or 40, wherein the instructions further indicate the VEGF antagonist is administered on an as needed basis, i.e., pro re nata (PRN), at the discretion of a treatment provider (e.g., a physician or other qualified medical professional) based on visual and/or anatomical outcomes to determine disease activity before or after any q12w dose.

44. A method for preventing progression of proliferative diabetic retinopathy (PDR) to non-proliferative diabetic retinopathy (NPDR) in a patient, the method comprising:
   a) administering to the patient three individual doses of a VEGF antagonist at 6-week intervals; and
   b) administering to the patient an additional dose of the VEGF antagonist once every 12 weeks (q12w regimen) thereafter.
45. The method of embodiment 44, further comprising assessing the patient for disease activity before or after administering every q12w dose.
46. The method of embodiment 45, wherein disease activity is assessed based on identifying best corrected visual acuity (BCVA), ETDRS DRSS score, retinal neovascularization status, and peripheral visual field.
47. The method of embodiment 45 or 46, wherein if worsening of disease activity is identified after a q12w dose, the patient is switched to a q6w regimen, wherein the additional doses are administered once every 6 weeks instead of once every 12 weeks.
48. The method of embodiment 47, wherein the worsening of disease activity is new or worsening retinal neovascularization, reperfusion of retinal neovascularization, increase in ETDRS DRSS score (such as an increase of 2 or more steps), loss in peripheral visual field, and/or developing complications that impact visual acuity compared to any previous assessment.
49. The method of any one of embodiments 45 to 46, wherein at week 48 after the first dose was administered, the q12w treatment interval is extended by 6 weeks at a time up to 24 weeks (q24w).
50. The method of any one of embodiments 44-49, wherein the patient is a human.
51. The method of any one of embodiments 44-50, wherein the anti-VEGF antagonist comprises the sequence of SEQ ID NO: 3.
52. The method of any one of embodiments 44-51, wherein the VEGF antagonist is administered by intravitreal injection.
53. The method of any one of embodiments 44-52, wherein the wherein the dose of the VEGF antagonist is about 3 mg to about 6 mg.

Specific preferred embodiments of the invention will become evident from the following more detailed description of certain preferred embodiments and the claims.

DETAILED DESCRIPTION

Definitions

The following definitions and explanations are meant and intended to be controlling in any future construction unless clearly and unambiguously modified in the following examples or when application of the meaning renders any construction meaningless or essentially meaningless. In cases where the construction of the term would render it meaningless or essentially meaningless, the definition should be taken from Webster's Dictionary, 3rd Edition or a dictionary known to those of skill in the art, such as the Oxford Dictionary of Biochemistry and Molecular Biology (Ed. Anthony Smith, Oxford University Press, Oxford, 2004).

As used herein, all percentages are percentages by weight, unless stated otherwise.

As used herein and unless otherwise indicated, the terms "a" and "an" are taken to mean "one", "at least one" or "one or more". Unless otherwise required by context, singular terms used herein shall include pluralities and plural terms shall include the singular.

The contents of any patents, patent applications, and references cited throughout this specification are hereby incorporated by reference in their entireties.

The term "VEGF" refers to the 165-amino acid vascular endothelial cell growth factor, and related 121-, 189-, and 206-amino acid vascular endothelial cell growth factors, as described by Leung et al., Science 246:1306 (1989), and Houck et al., Mol. Endocrin. 5:1806 (1991) together with the naturally occurring allelic and processed forms of those growth factors.

The term "VEGF receptor" or "VEGFr" refers to a cellular receptor for VEGF, ordinarily a cell-surface receptor found on vascular endothelial cells, as well as variants thereof retaining the ability to bind hVEGF. One example of a VEGF receptor is the fms-like tyrosine kinase (flt), a transmembrane receptor in the tyrosine kinase family. DeVries et al., Science 255:989 (1992); Shibuya et al., Oncogene 5:519 (1990). The flt receptor comprises an extracellular domain, a transmembrane domain, and an intracellular domain with tyrosine kinase activity. The extracellular domain is involved in the binding of VEGF, whereas the intracellular domain is involved in signal transduction. Another example of a VEGF receptor is the flk-1 receptor (also referred to as KDR). Matthews et al., Proc. Nat. Acad. Sci. 88:9026 (1991); Terman et al., Oncogene 6:1677 (1991); Terman et al., Biochem. Biophys. Res. Commun. 187:1579 (1992). Binding of VEGF to the flt receptor results in the formation of at least two high molecular weight complexes, having an apparent molecular weight of 205,000 and 300,000 Daltons. The 300,000 Dalton complex is believed to be a dimer comprising two receptor molecules bound to a single molecule of VEGF.

As used herein, a "VEGF antagonist" refers to a compound that can diminish or inhibit VEGF activity in vivo. A VEGF antagonist can bind to a VEGF receptor(s) or block VEGF protein(s) from binding to VEGF receptor(s). A VEGF antagonist can be, for example, a small molecule, an anti-VEGF antibody or antigen-binding fragments thereof, fusion protein (such as aflibercept or other such soluble decoy receptor), an aptamer, an antisense nucleic acid molecule, an interfering RNA, receptor proteins, and the like that can bind specifically to one or more VEGF proteins or one or more VEGF receptors. Several VEGF antagonists are described in WO 2006/047325.

In a preferred embodiment, the VEGF antagonist is an anti-VEGF antibody (such as brolucizumab or ranibizumab or bevacizumab or a bi-specific antibody such as faricimab) or a soluble VEGF receptor (such as aflibercept).

The term "antibody" as used herein includes whole antibodies and any antigen binding fragment (i.e., "antigen-binding portion," "antigen binding polypeptide," or "immunobinder") or single chain thereof. An "antibody" includes a glycoprotein comprising at least two heavy (H) chains and two light (L) chains inter-connected by disulfide bonds, or an antigen binding portion thereof. Each heavy chain is comprised of a heavy chain variable region (abbreviated herein as $V_H$) and a heavy chain constant region. The heavy chain constant region is comprised of three domains, CH1, CH2 and CH3. Each light chain is comprised of a light chain variable region (abbreviated herein as $V_L$) and a light chain constant region. The light chain constant region is comprised of one domain, CL. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

The term "single chain antibody", "single chain Fv" or "scFv" is intended to refer to a molecule comprising an antibody heavy chain variable domain (or region; $V_H$) and an antibody light chain variable domain (or region; $V_L$) connected by a linker. Such scFv molecules can have the general structures: $NH_2$—$V_L$-linker-$V_H$—COOH or $NH_2$—$V_H$-linker-$V_L$—COOH.

The term "antigen-binding portion" of an antibody (or simply "antibody portion") refers to one or more fragments of an antibody that retain the ability to specifically bind to an antigen (e.g., VEGF). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the $V_L$, $V_H$, CL and CH1 domains; (ii) a $F(ab')_2$ fragment, a bivalent fragment comprising two Fab fragments linked by a disulfide bridge at the hinge region; (iii) a Fd fragment consisting of the $V_H$ and CH1 domains; (iv) a Fv fragment consisting of the $V_L$ and $V_H$ domains of a single arm of an antibody, (v) a single domain or dAb fragment (Ward et al., (1989) Nature 341: 544-546), which consists of a $V_H$ domain; and (vi) an isolated complementarity determining region (CDR) or (vii) a combination of two or more isolated CDRs which may optionally be joined by a synthetic linker. Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies. Antigen-binding portions can be produced by recombinant DNA techniques, or by enzymatic or chemical cleavage of intact immunoglobulins. Antibodies can be of different isotype, for example, an IgG (e.g., an IgG1, IgG2, IgG3, or IgG4 subtype), IgA1, IgA2, IgD, IgE, or IgM antibody.

As used herein, a "mammal" includes any animal classified as a mammal, including, but not limited to, humans, domestic animals, farm animals, and companion animals, etc.

An "ocular disease" or "neovascular ocular disease" that can be treated using a method of the invention includes, a condition, disease, or disorder associated with ocular neovascularization, including, but not limited to, abnormal angiogenesis, choroidal neovascularization (CNV), retinal vascular permeability, retinal edema, diabetic retinopathy (particularly proliferative diabetic retinopathy (PDR) and non-proliferative diabetic retinopathy (NPDR)), diabetic macular edema (DME), neovascular (exudative) age-related macular degeneration (AMD), including CNV associated with nAMD (neovascular AMD), sequela associated with retinal ischemia, Central Retinal Vein Occlusion (CRVO), Branch Retinal Vein Occlusion (BRVO), and posterior segment neovascularization. In a preferred embodiment, the disease is PDR. In another preferred embodiment, the disease is NPDR.

As used herein, the term "subject" or "patient" refers to human and non-human mammals, including but, not limited to, primates, pigs, horses, dogs, cats, sheep, and cows. Preferably, a subject or patient is a human.

Treatment Regimen

In one aspect, the invention provides methods for treating a patient having diabetic retinopathy (DR), non-proliferative diabetic retinopathy (NPDR), and proliferative diabetic retinopathy (PDR), the method comprising administering to the patient a VEGF antagonist on a treatment schedule that includes a loading phase and a maintenance phase as described herein. In certain embodiments the invention provides methods for preventing progression of NPDR to PDR, the comprising administering to the patient a VEGF antagonist on a treatment schedule that includes a loading phase and a maintenance phase as described herein.

In certain embodiments, a patient is at least 18 years of age, and has been diagnosed with diabetes mellitus (DM) type 1 or 2, and HbA1c≤12%. In other embodiments, a patient has PDR as assessed by a treatment provider, and has a BCVA≥34 ETDRS letters (Snellen equivalent 20/200). A patient is diagnosed with PDR by a treatment provider, for example, using standard or wide-field Color Fundus Photographs (CFP), optionally fluorescein angiography (FA). In other embodiments, a patient has not received panretinal photocoagulation (PRP) laser treatment.

In certain embodiments, the loading phase consists of at least two individual doses, administered at 6-week intervals (q6w), e.g., at day 0, at week 6, and at week 12. In certain embodiments, the maintenance phase starts with a dosing regimen wherein the VEGF antagonist is administered once every 12-weeks (q12w), and the dosing interval is adjusted plus or minus 6-weeks depending a disease activity assessment conducted before a dose is administered. In one embodiment, if disease activity is observed prior to administering a q12w dose, the patient will receive the q12w dose as planned, and receive the next dose 6 weeks later, thus being placed on a q6w dosing regimen until disease activity is no longer observed. When disease activity is no longer observed, the dosing regimen will be adjusted back to a q12w schedule. In another embodiment, if no disease activity is observed at any time during the maintenance phase, the treatment interval may be extended by 6 weeks to a q18w, and an additional 6 weeks thereafter to 24 weeks (q24w) interval. If disease activity is observed in a patient on a q24w dosing regimen, the treatment interval may be adjusted back to a q18w or q12w dosing regimen.

In one aspect, the invention provides methods for treating ocular neovascular diseases, including PDR, in a mammal, the methods comprising administering multiple doses of a VEGF antagonist (e.g., anti-VEGF antibody or fragment thereof) to the mammal at various intervals for at least two years. In certain embodiments, the doses are administered at two or three 6-week intervals, the "loading phase," followed by administering additional doses at 6-week, 7-week, 8-week, 9-week, 10-week, 11-week, 12-week, 13-week, 14-week, 15-week, 16-week, 17-week, 18-week, 19-week, 20-week, 21-week, 22-week, 23-week, or 24-week intervals during the "maintenance phase." Disease activity assessments are conducted at least at every additional scheduled administration during the maintenance phase. When disease activity is identified as described herein, the treatment regimen can be changed from every 12 weeks to every 6 weeks (i.e., q6w). The invention provides specific criteria established by the inventors based on disease activity assessments to determine when an 6-week interval should be used and when a 12-week interval should be continued. In some cases, a patient might be on a 12-week interval regimen for some time, and then switch to a 6-week interval, and then switch back to the 12-week interval. Thus, patients may not stay on one interval regimen, and may go back and forth depending on assessments according to the criteria set forth herein.

In one embodiment, when disease activity is not detected for multiple consecutive treatment visits, the treatment provider can extend treatment an additional one to 24 weeks. For example, if a patient is being treated every 12 weeks, the treatment provider may extend treatments to every 13, 14, 15, 16, 17, 18, 19, 20, 21, 22, 23, or 24 weeks; or if a patient is being treated every 6 weeks, the treatment provider may extend treatments to every 7, 8, 9, 10, 11, or 12 weeks. If disease activity is identified at any treatment visit, the treatment schedule is adjusted back to the 12 week or 6 week treatment regimen. As used herein, "disease activity" refers to worsening of the ocular disease based on criteria provided herein.

In one embodiment, the invention provides a method for treating ocular diseases, particularly ocular neovascular diseases, more particularly PDR, comprising administering a VEGF antagonist to a mammal in need thereof according to the following schedule:

a "loading phase" of 3 doses administered at 6-week (i.e., "q6" or "q6w") intervals (e.g., day 0, week 6, week 12), and a "maintenance phase" of additional doses administered at 12-week (i.e., "q12" or "q12w") intervals.

In certain embodiments, the "maintenance phase" can be additional doses at 6, 7, 8, 9, 10, 11, 12, 13, 14, 15, 16, 17, 18, 19, 20, 21, 22, 23, or 24 week intervals, and can be adjusted as described herein based on Disease Activity Assessments as described herein.

In certain embodiments, the "loading phase" can be 2, 3, 4, 5, or 6 doses administered at q6w intervals. In other embodiments, the "loading phase can be 2, 3, 4, 5, or 6 doses administered once every four weeks (q4w intervals).

In certain embodiments, a Disease Activity Assessment ("DAA") is conducted at all scheduled treatment visits. In one embodiment, a patient is reassigned to q6w or q12w dosing regimen based on the presence of disease activity as determined by a treatment provider, for example new or worsening retinal neovascularization, reperfusion of retinal neovascularization, increase in ETDRS DRSS score (such as an increase of 2 or more steps for DR disease activity), loss in peripheral visual field, and/or developing complications that impact visual acuity compared to any previous assessment.

At assessment weeks, the patients can be currently on, for example, a 6-week or 12-week or 24-week interval regimen. Thus, the assessment can determine if a patient stays on the current interval or switches to a different interval.

In certain embodiments, the VEGF antagonist used in a method of the invention is brolucizumab, and is administered at a dose of 1, 2, 3, 4, 5, or 6 mg (e.g., 6 mg/0.05 mL) as an intravitreal injection.

An assessment as described herein preferably includes one or more of the following tests to assess activity of a VEGF antagonist (e.g., brolucizumab) on visual function, retinal structure and leakage:

Best-corrected visual acuity with ETDRS-like chart at 4 meters

ETDRS DRSS score based on 7-field stereo Color Fundus Photography (CFP)

Anatomical retinal evaluation by Optical Coherence Tomography (OCT), standard or wide-field Fluorescein Angiography (FA), OCT angiography, and/or wide-field CFP/FA Peripheral visual field assessed by perimetry Contrast sensitivity Visual acuity can be assessed using best correction determined from protocol refraction (BCVA). BCVA measurements can be taken, for example, in a sitting position using ETDRS-like visual acuity testing charts.

Optical Coherence Tomography (OCT), color fundus photography and fluorescein angiography can be assessed according to methods known to those of skill in the art.

Additional criteria for assessing disease activity includes, but is not limited to, changes in central subfield thickness (CST). The CST is the average thickness of circular 1 mm area centered around the fovea measured from retinal pigment epithelium (RPE) to the internal limiting membrane (ILM), inclusively. CST can be measured, for example, using spectral domain Optical Coherence Tomography (SD-OCT).

Means of performing the above tests are well understood and commonly used by those skilled in the art.

Disease activity is assessed for clinically relevant improvements of BCVA, reduction of central subfield thickness (CST), reduction of fluid accumulation (e.g., retinal fluid) and/or decreased severity of diabetic retinopathy. Where disease activity is worsening (for example, loss of letters measured by BCVA, increase in CST, increased fluid accumulation, and or increased severity of diabetic retinopathy compared with baseline reading for the patient or compared with any previous assessment), a more frequent dosing interval is prescribed going forward. Where improvement of disease activity is observed, a less frequent dosing interval is prescribed. Where there is neither worsening nor improvement of disease activity (i.e. the patient's disease is stable), the dosing interval is maintained or extended (less frequent). Fluid measured in the eye can be intraretinal and/or subretinal fluid.

Assessing status of disease activity can be based, for example, on dynamic changes (e.g., a decreased measurement compared with a previous assessment, such as the baseline assessment) in diabetic retinopathy severity (e.g. retinal neovascularization) based on ophthalmoscopy, standard or wide-field color fundus photography and/or standard or wide-field Fluorescein Angiography (FA) and/or OCT angiography, BCVA, ETDRS DRSS score based on 7-field stereo Color Fundus Photography (CFP), anatomical retinal evaluation by Optical Coherence Tomography (OCT), peripheral visual field assessed by perimetry and/or contrast sensitivity. Thereafter, guidance can be based, for example, on BCVA decline due to disease activity compared with a previous assessment. It should be understood the treating clinician can make a decision based on clinical judgment, which can include more than visual acuity criteria. Disease activity assessments can include both visual acuity and anatomical criteria. In certain embodiments, disease activity is assessed when the following are observed: new or worsening retinal neovascularization, reperfusion of retinal neovascularization, increase in ETDRS DRSS score (such as an increase of 2 or more steps for DR disease activity), loss in peripheral visual field, and/or developing complications that impact visual acuity compared to any previous assessment.

In one embodiment, assessments of disease activity to establish the patient's disease status occurs at baseline (Week 0; first treatment). The assessment of the disease activity (DAA) during treatment regimens is at the discretion of the person making the assessment (e.g., the treatment provider), and is based on changes in vision and anatomical and morphological and clinical parameters with reference to the patients' baseline disease status (at Week 0).

In certain other embodiments, during the maintenance phase, the VEGF antagonist is administered on an as needed basis, i.e., pro re nata (PRN), at the discretion of a treatment provider (e.g., a physician or other qualified medical professional) based on visual and/or anatomical outcomes to determine disease activity.

Anti-VEGF Antagonists

In certain embodiments, a VEGF antagonist used in a method of the invention is an anti-VEGF antibody, particularly anti-VEGF antibodies described in WO 2009/155724, the entire contents of which are hereby incorporated by reference.

In one embodiment, an anti-VEGF antibody used in a method of the invention comprises a variable heavy chain having the sequence as set forth in SEQ ID NO: 1 and a variable light chain having the sequence as set forth in SEQ ID NO: 2.

VH:

SEQ ID NO. 1

EVQLVESGGGLVQPGGSLRLSCTASGFSLTDYYYMTWVRQAPGKGLEWVG

FIDPDDDPYYATWAKGRFTISRDNSKNTLYLQMNSLRAEDTAVYYCAGGD

HNSGWGLDIWGQGTLVTVSS

VL:

SEQ ID NO. 2

EIVMTQSPSTLSASVGDRVIITCQASEIIHSWLAWYQQKPGKAPKLLIYL

ASTLASGVPSRFSGSGSGAEFTLTISSLQPDDFATYYCQNVYLASTNGAN

FGQGTKLTVLG

In another embodiment, the anti-VEGF antibody used in a method of the invention comprises the sequence as set forth in SEQ ID NO: 3.

EIVMTQSPSTLSASVGDRVIITCQASEIIHSWLAWYQQKPGKAPKLLIYL

ASTLASGVPSRFSGSGSGAEFTLTISSLQPDDFATYYCQNVYLASTNGAN

FGQGTKLTVLGGGGGSGGGGSGGGGSGGGGSEVQLVESGGGLVQPGGSLR

LSCTASGFSLTDYYYMTWVRQAPGKGLEWVGFIDPDDDPYYATWAKGRFT

ISRDNSKNTLYLQMNSLRAEDTAVYYCAGGDHNSGWGLDIWGQGTLVTVS

S

In a preferred embodiment, the anti-VEGF antibody used in a method of the invention (e.g, a method treating DR or PDR or preventing progression of nPDR to PDR) is brolucizumab (which comprises the sequence of SEQ ID NO: 3). The sequence of brolucizumab is set forth in SEQ ID NO: 4. A methionine derived from the start codon in an expression vector is present in the final protein in cases where it has not been cleaved posttranslationally as follows.

(SEQ ID NO: 4)

MEIVMTQSPS TLSASVGDRV IITCQASEII HSWLAWYQQK PGKAPKLLIY LASTLASGVP

SRFSGSGSGA EFTLTISSLQ PDDFATYYCQ NVYLASTNGA NFGQGTKLTV LGGGGGSGGG

GSGGGGSGGG GSEVQLVESG GGLVQPGGSL RLSCTASGES LTDYYYMTWV RQAPGKGLEW

VGFIDPDDDP YYATWAKGRF TISRDNSKNT LYLQMNSLRA EDTAVYYCAG GDHNSGWGLD

IWGQGTLVTV SS

In another embodiment, an anti-VEGF antibody used in a method of the invention comprises three light chain CDRs (CDRL1, CDRL2, and CDRL3) and three heavy chain CDRs (CDRH1, a CDRH2, a CDRH3) as follows:

```
                                   SEQ ID NO: 5
        CDRL1 QASEIIHSWLA

SEQ ID NO: 6
        CDRL2 LASTLAS

SEQ ID NO: 7
        CDRL3 QNVYLASTNGAN

SEQ ID NO: 8
        CDRH1 GFSLTDYYYMT

SEQ ID NO: 9
        CDRH2 FIDPDDDPYYATWAKG

SEQ ID NO: 10
        CDRH3 GDHNSGWGLDI
```

Brolucizumab, is a humanized single-chain Fv (scFv) antibody fragment inhibitor of VEGF with a molecular weight of ~26 kDa. It is an inhibitor of VEGF-A and works by binding to the receptor binding site of the VEGF-A molecule, thereby preventing the interaction of VEGF-A with its receptors VEGFR1 and VEGFR2 on the surface of endothelial cells. Increased levels of signaling through the VEGF pathway are associated with pathologic ocular angiogenesis and retinal edema. Inhibition of the VEGF pathway has been shown to inhibit the growth of neovascular lesions and resolve retinal edema in patients with nAMD.

Pharmaceutical Preparations

In one aspect the methods of the invention comprise the use of pharmaceutical formulations comprising anti-VEGF antibodies. The term "pharmaceutical formulation" refers to preparations which are in such form as to permit the biological activity of the antibody or antibody derivative to be unequivocally effective, and which contain no additional components which are toxic to the subjects to which the formulation would be administered. "Pharmaceutically acceptable" excipients (vehicles, additives) are those which can reasonably be administered to a subject mammal to provide an effective dose of the active ingredient employed.

A "stable" formulation is one in which a therapeutic agent, e.g. an anti-VEGF antibody or antibody derivative thereof essentially retains its physical stability and/or chemical stability and/or biological activity upon storage. Various analytical techniques for measuring protein stability are available in the art and are reviewed in Peptide and Protein Drug Delivery, 247-301, Vincent Lee Ed., Marcel Dekker, Inc., New York, N.Y., Pubs. (1991) and Jones, A. Adv. Drug Delivery Rev. 10: 29-90 (1993), for example. Stability can be measured at a selected temperature for a selected time period. Preferably, the formulation is stable at room temperature (about 30° C.) or at 40° C. for at least 1 week and/or stable at about 2-8° C. for at least 3 months to 2 years. Furthermore, the formulation is preferably stable following freezing (to, e.g., −70° C.) and thawing of the formulation.

An antibody or antibody derivative "retains its physical stability" in a pharmaceutical formulation if it meets the defined release specifications for aggregation, degradation, precipitation and/or denaturation upon visual examination of color and/or clarity, or as measured by UV light scattering or by size exclusion chromatography, or other suitable art recognized methods.

An antibody or antibody derivative "retains its chemical stability" in a pharmaceutical formulation, if the chemical stability at a given time is such that the protein is considered to still retain its biological activity as defined below. Chemical stability can be assessed by detecting and quantifying chemically altered forms of the protein. Chemical alteration may involve size modification (e.g. clipping) which can be evaluated using size exclusion chromatography, SDS-PAGE and/or matrix-assisted laser desorption ionization/time-of-flight mass spectrometry (MALDI/TOF MS), for example. Other types of chemical alteration include charge alteration (e.g. occurring as a result of deamidation) which can be evaluated by ion-exchange chromatography, for example.

An antibody or antibody derivative "retains its biological activity" in a pharmaceutical formulation, if the biological activity of the antibody at a given time is within about 10% (within the errors of the assay) of the biological activity exhibited at the time the pharmaceutical formulation was prepared as determined in an antigen binding assay, for example. Other "biological activity" assays for antibodies are elaborated herein below.

By "isotonic" is meant that the formulation of interest has essentially the same osmotic pressure as human blood. Isotonic formulations will generally have an osmotic pressure from about 250 to 350 mOsm. Isotonicity can be measured using a vapor pressure or ice-freezing type osmometer, for example.

A "polyol" is a substance with multiple hydroxyl groups, and includes sugars (reducing and non-reducing sugars), sugar alcohols and sugar acids. Preferred polyols herein have a molecular weight which is less than about 600 kD (e.g. in the range from about 120 to about 400 kD). A "reducing sugar" is one which contains a hemiacetal group that can reduce metal ions or react covalently with lysine and other amino groups in proteins and a "non-reducing sugar" is one which does not have these properties of a reducing sugar. Examples of reducing sugars are fructose, mannose, maltose, lactose, arabinose, xylose, ribose, rhamnose, galactose and glucose. Non-reducing sugars include sucrose, trehalose, sorbose, melezitose and raffinose. Mannitol, xylitol, erythritol, threitol, sorbitol and glycerol are examples of sugar alcohols. As to sugar acids, these include L-gluconate and metallic salts thereof. Where it is desired that the formulation is freeze-thaw stable, the polyol is preferably one which does not crystallize at freezing temperatures (e.g. −20° C.) such that it destabilizes the antibody in the formulation. Non-reducing sugars such as sucrose and trehalose are the preferred polyols herein, with trehalose being preferred over sucrose, because of the superior solution stability of trehalose.

As used herein, "buffer" refers to a buffered solution that resists changes in pH by the action of its acid-base conjugate components. The buffer of this invention has a pH in the range from about 4.5 to about 8.0; preferably from about 5.5 to about 7. Examples of buffers that will control the pH in this range include acetate (e.g. sodium acetate), succinate (such as sodium succinate), gluconate, histidine, citrate and other organic acid buffers. Where a freeze-thaw stable formulation is desired, the buffer is preferably not phosphate.

In a pharmacological sense, in the context of the present invention, a "therapeutically effective amount" of a therapeutic agent, e.g. an anti-VEGF antibody or antibody derivative refers to an amount effective in the prevention or treatment of a disorder for the treatment of which the antibody or antibody derivative is effective. This includes chronic and acute disorders or diseases including those pathological conditions which predispose the mammal to the disorder in question.

A "preservative" is a compound which can be included in the formulation to essentially reduce bacterial action therein, thus facilitating the production of a multi-use formulation, for example. Examples of potential preservatives include octadecyldimethylbenzyl ammonium chloride, hexamethonium chloride, benzalkonium chloride (a mixture of alkylbenzyldimethylammonium chlorides in which the alkyl groups are long-chain compounds), and benzethonium chloride. Other types of preservatives include aromatic alcohols such as phenol, butyl and benzyl alcohol, alkyl parabens such as methyl or propyl paraben, catechol, resorcinol, cyclohexanol, 3-pentanol, and m-cresol. The most preferred preservative herein is benzyl alcohol.

The pharmaceutical compositions used in present invention comprise a VEGF antagonist, preferably an anti-VEGF antibody (e.g., an anti-VEGF antibody comprising the variable light chain sequence of SEQ ID NO: 1 and the variable heavy chain sequence of SEQ ID NO: 2, such as brolucizumab), together with at least one physiologically acceptable carrier or excipient. Pharmaceutical compositions may comprise, for example, one or more of water, buffers (e.g., neutral buffered saline or phosphate buffered saline), ethanol, mineral oil, vegetable oil, dimethylsulfoxide, carbohydrates (e.g., glucose, mannose, sucrose or dextrans), mannitol, proteins, adjuvants, polypeptides or amino acids such as glycine, antioxidants, chelating agents such as EDTA or glutathione and/or preservatives. As noted above, other active ingredients may (but need not) be included in the pharmaceutical compositions provided herein.

A carrier is a substance that may be associated with an antibody or antibody derivative prior to administration to a patient, often for the purpose of controlling stability or bioavailability of the compound. Carriers for use within such formulations are generally biocompatible, and may also be biodegradable. Carriers include, for example, monovalent or multivalent molecules such as serum albumin (e.g., human or bovine), egg albumin, peptides, polylysine and polysaccharides such as aminodextran and polyamidoamines. Carriers also include solid support materials such as beads and microparticles comprising, for example, polylactate polyglycolate, poly(lactide-co-glycolide), polyacrylate, latex, starch, cellulose or dextran. A carrier may bear the compounds in a variety of ways, including covalent bonding (either directly or via a linker group), noncovalent interaction or admixture.

Pharmaceutical compositions may be formulated for any appropriate manner of administration, including, for example, topical, intraocular, oral, nasal, rectal or parenteral administration. In certain embodiments, compositions in a form suitable for intraocular injection, such as intravitreal injection, are preferred. Other forms include, for example, pills, tablets, troches, lozenges, aqueous or oily suspensions, dispersible powders or granules, emulsion, hard or soft capsules, or syrups or elixirs. Within yet other embodiments, compositions provided herein may be formulated as a lyophilizate. The term parenteral as used herein includes subcutaneous, intradermal, intravascular (e.g., intravenous), intramuscular, spinal, intracranial, intrathecal and intraperitoneal injection, as well as any similar injection or infusion technique.

The pharmaceutical composition may be prepared as a sterile injectible aqueous or oleaginous suspension in which the active agent (i.e. VEGF antagonist), depending on the vehicle and concentration used, is either suspended or dissolved in the vehicle. Such a composition may be formulated according to the known art using suitable dispersing, wetting agents and/or suspending agents such as those mentioned above. Among the acceptable vehicles and solvents that may be employed are water, 1,3-butanediol, Ringer's solution and isotonic sodium chloride solution. In addition, sterile, fixed oils may be employed as a solvent or suspending medium. For this purpose any bland fixed oil may be employed, including synthetic mono- or diglycerides. In addition, fatty acids such as oleic acid may be used in the preparation of injectible compositions, and adjuvants such as local anesthetics, preservatives and/or buffering agents can be dissolved in the vehicle.

Dosage

A dose used in a method of the invention is based on the specific disease or condition being treated. The term "therapeutically effective dose" is defined as an amount sufficient to achieve or at least partially achieve the desired effect (e.g. the partial or complete regression of retinal neovascularization, a change of BCVA>1, >2, >3, >4 or >5 letters, or a DRSS score <61). A therapeutically effective dose is sufficient if it can produce even an incremental change in the symptoms or conditions associated with the disease. The therapeutically effective dose does not have to completely cure the disease or completely eliminate symptoms. Preferably, the therapeutically effective dose can at least partially arrest the disease and/or its complications in a patient already suffering from the disease. Amounts effective for this use will depend upon the severity of the disorder being treated and the general state of the patient's own immune system.

The dose amount can be readily determined using known dosage adjustment techniques by a physician having ordinary skill in treatment of the disease or condition. The therapeutically effective amount of a VEGF antagonist used in a method of the invention is determined by taking into account the desired dose volumes and mode(s) of administration, for example. Typically, therapeutically effective compositions are administered in a dosage ranging from 0.001 mg/ml to about 200 mg/ml per dose. Preferably, a dosage used in a method of the invention is about 60 mg/ml to about 120 mg/ml (for example, a dosage is 60, 70, 80, 90, 100, 110, or 120 mg/ml). In a preferred embodiment, the dosage of an anti-VEGF antibody used in a method of the invention (e.g., a method of treating DR or PDR or preventing progression of nPDR to PDR) is 60 mg/ml or 120 mg/ml.

In certain embodiments, a dose is administered directly to an eye of a patient. In one embodiment, a dose per eye is at least about 0.5 mg up to about 6 mg. Preferred doses per eye include about 0.5 mg, 0.6 mg, 0.7 mg, 0.8 mg, 0.9 mg, 1.0 mg, 1.2 mg, 1.4 mg, 1.6 mg, 1.8 mg, 2.0 mg, 2.5 mg, 3.0 mg, 3.5 mg, 4.0 mg, 4.5 mg, 5.0 mg, 5.5 mg, and 6.0 mg. In one embodiment, a dose per eye is at least about 3 mg up to about 6 mg, in particular about 3 mg or about 6 mg. Doses can be administered in various volumes suitable for ophthalmic administration, such as 50 μl or 100 μl, for example, including 3 mg/50 μl or 6 mg/50 μl. Smaller volumes can also be used, including 20 μl or less, for example about 20 μl, about 10 μl, or about 8.0 μl. In certain embodiments, a dose of 2.4 mg/20 μl, 1.2 mg/10 μl or 1 mg/8.0 μl (e.g., 1 mg/8.3 μl) is delivered to an eye of a patient for treating or ameliorating one or more of the diseases and disorders described above. Delivery can be, for example, by intravitreal injection.

As used herein, the term "about" includes and describes the value or parameter per se. For example, "about x" includes and describes "x" per se. As used herein, the term "about" when used in association with a measurement, or used to modify a value, a unit, a constant, or a range of values, refers to variations of ±1-10% in addition to including the value or parameter per se. In some embodiments, the term "about" when used in association with a measurement, or used to modify a value, a unit, a constant, or a range of values, refers to variations of ±1, ±2, ±3, ±4, ±5, ±6, ±7, ±8, ±9, or ±10%.

An aqueous formulation of an anti-VEGF antibody used in a method of the invention is prepared in a pH-buffered solution. Preferably, the buffer of such aqueous formulation has a pH in the range from about 4.5 to about 8.0, preferably from about 5.5 to about 7.0, most preferably about 6.75. In one embodiment, the pH of an aqueous pharmaceutical composition of the invention is about 7.0-7.5, or about 7.0-7.4, about 7.0-7.3, about 7.0-7.2, about 7.1-7.6, about 7.2-7.6, about 7.3-7.6 or about 7.4-7.6. In one embodiment, an aqueous pharmaceutical composition of the invention has a pH of about 7.0, about 7.1, about 7.2, about 7.3, about 7.4, about 7.5 or about 7.6. In a preferred embodiment, the aqueous pharmaceutical composition has a pH of ≥7.0 In a preferred embodiment, the aqueous pharmaceutical composition has a pH of about 7.2. In another preferred embodiment, the aqueous pharmaceutical composition has a pH of about 7.4. In another preferred embodiment, the aqueous pharmaceutical composition has a pH of about 7.6. Examples of buffers that will control the pH within this range include acetate (e.g. sodium acetate), succinate (such as sodium succinate), gluconate, histidine, citrate and other organic acid buffers. The buffer concentration can be from about 1 mM to about 50 mM, preferably from about 5 mM to about 30 mM, depending, for example, on the buffer and the desired isotonicity of the formulation.

A polyol, which acts as a tonicifier, may be used to stabilize an antibody in an aqueous formulation. In preferred embodiments, the polyol is a non-reducing sugar, such as sucrose or trehalose. If desired, the polyol is added to the formulation in an amount that may vary with respect to the desired isotonicity of the formulation. Preferably the aqueous formulation is isotonic, in which case suitable concentrations of the polyol in the formulation are in the range from about 1% to about 15% w/v, preferably in the range from about 2% to about 10% w/v, for example. However, hypertonic or hypotonic formulations may also be suitable. The amount of polyol added may also alter with respect to the molecular weight of the polyol. For example, a lower amount of a monosaccharide (e.g. mannitol) may be added, compared to a disaccharide (such as trehalose).

A surfactant is also added to an aqueous antibody formulation. Exemplary surfactants include nonionic surfactants such as polysorbates (e.g. polysorbates 20, 80 etc) or poloxamers (e.g. poloxamer 188). The amount of surfactant added is such that it reduces aggregation of the formulated antibody/antibody derivative and/or minimizes the formation of particulates in the formulation and/or reduces adsorption. For example, the surfactant may be present in the formulation in an amount from about 0.001% to about 0.5%, preferably from about 0.005% to about 0.2% and most preferably from about 0.01% to about 0.1%.

In one embodiment, an aqueous antibody formulation used in a method of the invention is essentially free of one or more preservatives, such as benzyl alcohol, phenol, m-cresol, chlorobutanol and benzethonium Cl. In another embodiment, a preservative may be included in the formulation, particularly where the formulation is a multidose formulation. The concentration of preservative may be in the range from about 0.1% to about 2%, most preferably from about 0.5% to about 1%. One or more other pharmaceutically acceptable carriers, excipients or stabilizers such as those described in Remington's Pharmaceutical Sciences 21st edition, Osol, A. Ed. (2006) may be included in the formulation provided that they do not adversely affect the desired characteristics of the formulation. Acceptable carriers, excipients or stabilizers are non-toxic to recipients at the dosages and concentrations employed and include: additional buffering agents, co-solvents, antioxidants including ascorbic acid and methionine, chelating agents such as EDTA, metal complexes (e.g. Zn-protein complexes), biodegradable polymers such as polyesters, and/or salt-forming counterions such as sodium.

Formulations to be used for in vivo administration must be sterile. This is readily accomplished by filtration through sterile filtration membranes, prior to, or following, preparation of the formulation.

In one embodiment, a VEGF antagonist is administered to an eye of a mammal in need of treatment in accordance with known methods for ocular delivery. Preferably, the mammal is a human, the VEGF antagonist is an anti-VEGF antibody (preferably brolucizumab), and the antibody is administered directly to an eye. Administration to a patient can be accomplished, for example, by intravitreal injection.

The VEGF antagonist in a method of the invention can be administered as the sole treatment or in conjunction with other drugs or therapies useful in treating the condition in question.

A preferred formulation for brolucizumab for intravitreal injection comprises about 4.5% to 11% (w/v) sucrose, 5-20 mM sodium citrate, and 0.001% to 0.05% (w/v) polysorbate 80, wherein the pH of the formulation is about 7.0 to about 7.4. One such formulation comprises 5.9% (w/v) sucrose, 10 mM sodium citrate, 0.02% (w/v) polysorbate 80, pH of 7.2, and 6 mg of brolucizumab. Another such formulation comprises 6.4% (w/v) or 5.8% sucrose, 12 mM or 10 mM sodium citrate, 0.02% (w/v) polysorbate 80, pH of 7.2, and 3 mg of brolucizumab. Preferred concentrations of brolucizumab are about 120 mg/ml and about 60 mg/ml. Doses can be delivered, for example as 6 mg/50 μL and 3 mg/50 μL concentrations.

Kits

The invention also provides a kit, comprising: a drug container (e.g., a vial or a prefilled syringe) comprising a VEGF antagonist drug (e.g., brolucizumab), and instructions for using the drug for treating a patient diagnosed with PDR. In one embodiment, the instructions indicate the drug is to be administered to the patient's eye in need thereof as follows: 3 doses of about 6 mg of VEGF antagonist administered at 6-week intervals followed by additional about 6 mg doses of the VEGF antagonist every 12 weeks. In certain embodiments, the instructions indicate the first 3 doses are administered in a "loading phase" and the additional doses are administered during a "maintenance phase."

In one embodiment, the kit comprises one or more 6 mg doses of brolucizumab, each dose provided in a single use vial containing sufficient brolucizumab to deliver a 6 mg dose when administering a volume of 0.05 mL or in a prefilled syringe containing 6 mg of brolucizumab.

In one embodiment, the instructions further indicate a treatment provider (e.g., a physician or other qualified medical professional) can adjust the dosing interval during the maintenance phase from once every 12 weeks to once every 6 weeks if disease activity is observed in the treated eye.

In another embodiment, the instructions further indicate a treatment provider (e.g., a physician or other qualified medical professional) can extend the dosing interval during the maintenance phase from once every 12 weeks to once every 24 weeks, 6 weeks at a time, if no disease activity is observed in the treated eye.

In yet another embodiment, the instructions further indicate the VEGF antagonist is administered on an as needed basis, i.e., pro re nata (PRN), at the discretion of a treatment provider (e.g., a physician or other qualified medical professional) based on visual and/or anatomical outcomes to determine disease activity during the maintenance phase.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Examples

A clinical study was designed to evaluate the efficacy and safety of brolucizumab, in particular compared to panretinal photocoagulation laser (PRP) in patients with proliferative diabetic retinopathy (PDR).

The study is a 96-week, two-arm, randomized, single-masked, multi-center, active-controlled, non-inferiority study in patients with proliferative diabetic retinopathy (PDR).

Patients who consent will undergo screening assessments to evaluate their eligibility based on certain inclusion and exclusion criteria. Subjects who meet all the inclusion and none of the exclusion criteria will be randomized 1:1:

Brolucizumab 6 mg: 3×q6w loading then q12w maintenance through Week 90, with the option from Week 48 onwards to extend the treatment interval by 6 weeks at a time up to 24 weeks.

PRP: initial treatment in 1-3 sessions up to Week 12, followed with additional PRP treatment as needed up to Week 90.

Visits will occur every 6 weeks throughout the study, regardless of treatment or not.

Brolucizumab Arm:

In the loading phase, treatment with brolucizumab occurs every 6 weeks for three (3) consecutive injections (Day 0 (Baseline), Week 6, and Week 12).

The treatment interval during the maintenance phase is as follows:

Patients receive q12w injections in the maintenance phase, i.e. at Week 24, Week 36, and Week 48 in the first year of treatment.

During the maintenance phase, the additional visits (e.g. Week 30) are planned for disease monitoring, not for treatment administration. However, additional injections may be administered at these visits at the treatment provider's discretion only if disease worsens, e.g. new or expanding retinal neovascularization compared to the previous visit. No injection should be administered if retinal neovascularization has been stable.

From Week 48 onwards,

The treatment interval may be extended by 6 weeks at a time, up to 24 weeks, at the treatment provider's discretion if, based on the treatment provider's assessment of disease activity, there is disease stability or regression, e.g. regressed or stabilized retinal neovascularization from the previous injection visit.

Thus, at Week 48 the treatment provider may elect to extend the treatment interval from 12 weeks to 18 weeks and treat the study eye at Week 66, if the disease did not worsen between Week 36 and Week 48 and there was no injection at Week 42. At Week 66, the treatment provider may elect to further extend the treatment interval from 18 weeks to 24 weeks, and treat the study eye at Week 90, if the disease did not worsen between Week 48 and Week 66, and there were no injections at Week 54 and Week 60.

The treatment provider may opt to revert to q12w injections if, in the treatment provider's opinion based on disease activity assessment, the patient needs more frequent treatment.

Brolucizumab will be provided either in a single use, sterile glass vial containing sufficient brolucizumab to deliver a 6 mg dose when administering a volume of 0.05 mL or in a prefilled syringe (PFS).

Brolucizumab is administered in the diseased eye on day 0 (Baseline). When assessments and treatments take place on the same day, treatment must occur after completion of the efficacy assessments described below.

PRP Arm:

Patients in the PRP arm will receive an initial treatment at Baseline. The treatment may be split into 2-3 sessions up to Week 12, as per local clinical practice. Additional PRP may be performed in the study eye if disease worsens, at the investigator's discretion, according to local practices.

Inclusion Criteria

Subjects eligible for inclusion in this study must meet all of the following criteria:

1. Signed informed consent must be obtained prior to participation in the study.
2. Patients ≥18 years of age at Screening.
3. Participant cooperation sufficient for adequate fundus photographs and retinal images.
4. Patients diagnosed with diabetes mellitus (DM) type 1 or 2, and HbA1c≤12% at Screening.
5. If taking medication for DM, medication for the management of diabetes must have been stable within 3 months prior to randomization and is expected to remain as stable as medically acceptable during the course of the study.

Study Eye

6. PDR as assessed by the investigator using standard or wide-field CFP, FA, with no evidence of previous PRP, and that requires treatment with either anti-VEGF or PRP in the opinion of the investigator.
7. BCVA≥34 ETDRS letters (Snellen equivalent 20/200).

Exclusion Criteria

Subjects meeting any of the following criteria are not eligible for inclusion in this study.

Ocular Conditions

1. Concomitant conditions or ocular disorders in the study eye at Screening or Baseline which, in the opinion of the investigator:
    a. could prevent functional or structural response to study treatment, or
    b. may confound interpretation of study results, or
    c. may compromise visual acuity, or
    d. require planned medical or surgical intervention during the first 54-week study period.

2. Presence of center-involved diabetic macular edema in the study eye at Screening or Baseline, as assessed by the investigator.

3. Any active intraocular or periocular infection or active intraocular inflammation (e.g. infectious conjunctivitis, keratitis, scleritis, infectious blepharitis, uveitis) in the study eye at Screening or Baseline.

4. Uncontrolled glaucoma in the study eye defined as intraocular pressure (IOP)>25 mmHg on medication, or according to investigator's judgment, at Screening or Baseline.

5. Moderate or dense pre-retinal or vitreous hemorrhage that prevents clear visualization of the macular and/or optic disc or prevents PRP treatment in the study eye at Baseline.

6. Fibrovascular proliferation or tractional retinal detachment in the posterior pole of the study eye.

7. Iris or anterior chamber angle neovascularization, or neovascular glaucoma in the study eye.

8. Presence of amblyopia, amaurosis or ocular disorders in the fellow eye with BCVA≤20/200 at screening (except when due to conditions for which surgery may improve VA, e.g. cataract).

Ocular Treatments in the Study Eye

9. PRP any time prior to Baseline.

10. Intravitreal anti-VEGF treatment within six months prior to Baseline.

11. Vitreoretinal surgery at any time prior to Baseline or anticipated need for vitreoretinal surgery within the next 12 months.

12. Laser treatment of the macula within three months prior to Baseline.

13. Treatment with fluocinolone acetonide intravitreal implant (e.g. ILUVIEN® or RETISERT®) at any time prior to Baseline. Other intraocular corticosteroid treatment within six months prior to Baseline.

14. Aphakia with the absence of posterior capsule.

15. Intraocular surgery within 3 months prior to Baseline or anticipated need for cataract extraction within the next 12 months.

Systemic Conditions and Treatments

16. Stroke or myocardial infarction during the 6-month period prior to baseline.

17. End stage renal disease requiring dialysis or renal transplant.

18. Uncontrolled blood pressure defined as a systolic value >180 mmHg or diastolic value >100 mmHg at screening or baseline. (In case there is an elevated blood pressure measurement, it should be repeated after 20 minutes. If the repeat measurement is elevated, then the patient is not eligible to be enrolled into the study).

19. Systemic anti-VEGF therapy at any time.

20. Systemic medications known to be toxic to the lens, retina or optic nerve (e.g., deferoxamine, chloroquine/hydroxychloroquine, tamoxifen, phenothiazines and ethambutol) used during the 6-month period prior to Baseline.

21. History of hypersensitivity to any of the study drugs or their excipients or to drugs of similar classes, or clinically relevant sensitivity to fluorescein dye as assessed by the investigator.

22. History of malignancy of any organ system (other than localized basal cell carcinoma of the skin or in situ cervical cancer), treated or untreated, within the past 5 years, regardless of whether there is evidence of local recurrence or metastases.

23. History of a medical condition (e.g., metabolic dysfunction disease with exception of type 1 or 2 diabetes mellitus, physical examination finding, or clinical laboratory finding) that, in the judgment of the investigator, would preclude scheduled study visits, completion of the study, or a safe administration of investigational product.

24. Use of systemic investigational drugs within 5 half-lives of baseline, or within 30 days/until the expected pharmacodynamic effect has returned to baseline, whichever is longer; or longer if required by local regulations (observational clinical studies solely involving over-the-counter vitamins, supplements, or diets are not exclusionary).

Other

25. Pregnant or nursing (lactating) women, where pregnancy is defined as the state of a female after conception and until the termination of gestation, confirmed by a positive human chorionic gonadotropin (hCG) pregnancy test.

26. Women of child-bearing potential, defined as all women physiologically capable of becoming pregnant, unless they are using highly effective methods of contraception during the study drug administration and for 22 days after stopping the investigational medication.

Efficacy (Disease Activity Assessment)

The following assessments will be performed to evaluate the effect of brolucizumab on visual function, diabetic retinopathy status, retinal and vascular structure:

Best-corrected visual acuity with ETDRS-like charts at 4 meters

ETDRS DRSS score based on 7-Field stereo Color Fundus Photography (CFP)

Anatomical retinal evaluation by SD-OCT, FA, OCT angiography, Wide-field CFP/FA

Peripheral visual field assessed by perimetry

All efficacy assessments are performed prior to any administration of treatment.

Visual Acuity

Visual acuity (VA) will be assessed in the study eye at every study visit and in the fellow eye at the Screening, Week 54 and Week 96/EOS visits using best correction determined from protocol refraction (BCVA). BCVA measurements will be taken in a sitting position using ETDRS-like visual acuity testing charts at an initial testing distance of 4 meters. The details of the refraction technique and VA testing, as well as training material, are provided in the applicable manual. Certification of the assessment procedures and assessors will occur prior to any evaluation of study subjects.

Color Fundus Photography and Fluorescein Angiography

Seven-Field stereo Color Fundus Photography (CFP) will be performed in both eyes at Baseline, Week 54, and Week 96 and in the treated eye at Week 18 and Week 72.

At sites that have the applicable equipment, optional Wide-Field (at least 100 degrees) Color Fundus Photography (WFCFP) should be performed in both eyes at Baseline, Week 54, and Week 96 and in the treated eye at Week 18 and Week 72. If WFCFP images were not taken at Baseline, they should not be introduced at later visits. WFCFP images will not replace 7-Field CFP images.

Standard or Wide-Field Fluorescein Angiography (FA) will be performed in the treated eye at the Baseline, Week 54, Week 96 visits and in the fellow eye at the Baseline visit. FA may be performed at other visits, at the treatment provider's discretion. The FA camera model used for an individual subject should not change for the duration of the treatment.

For the purpose of screening, FA images from a previous routine evaluation may be used as long as FA is performed within 3 days of the Baseline visit.

The treatment provider will evaluate the images according to their standard of clinical practice and may use any of the CFP, WFCFP, and FA imaging findings to inform his/her decision for treatment.

Optical Coherence Tomography

Spectral Domain Optical Coherence Tomography (SD-OCT) images will be obtained and assessed in both eyes at Baseline, Week 54 and Week 96 visits, and in the treated eye at all other visits.

These assessments will be performed by a trained technician or treatment provider at the sites and should be performed after BCVA assessment and prior to any treatment. Treatment providers will evaluate the SD-OCT images to assess the status of macular edema.

Only SD-OCT machines can be used (i.e. no time-domain nor swept-source OCT). The SD-OCT model used for an individual subject should not change for the duration of the treatment.

Central sub-field thickness (CSFT) will be measured by SD-OCT. The CSFT evaluated represents the average retinal thickness of the circular area within 1 mm diameter around the foveal center.

In addition to the standard SD-OCT assessment, when possible, wide-field or standard OCT angiography may be performed at each visit in the treated eye. If OCT angiography was not assessed at Baseline, then it should not be introduced at later visits. OCT angiography may be used by the treatment provider to complement the evaluation of retinal neovascularization as part of the disease activity assessment.

The treatment providers will evaluate the OCT images according to their clinical practice.

Peripheral Visual Field

Visual field examination in the treated eye will be performed at Baseline, Week 18, Week 54, Week 72, and Week 96 using automated perimetry. Visual field examination should be performed before treatment, if treatment is delivered at the visit. Accepted test methods are Humphrey 24-2, 30-2, and 60-4 with full-threshold and Swedish Interactive Thresholding Algorithm (SITA) standard strategies.

The present invention and its embodiments have been described in detail. However, the scope of the present invention is not intended to be limited to the particular embodiments of any process, manufacture, composition of matter, compounds, means, methods, and/or steps described in the specification. Various modifications, substitutions, and variations can be made to the disclosed material without departing from the spirit and/or essential characteristics of the present invention. Accordingly, one of ordinary skill in the art will readily appreciate from the disclosure that later modifications, substitutions, and/or variations performing substantially the same function or achieving substantially the same result as embodiments described herein may be utilized according to such related embodiments of the present invention. Thus, the following claims are intended to encompass within their scope modifications, substitutions, and variations to processes, manufactures, compositions of matter, compounds, means, methods, and/or steps disclosed herein. The claims should not be read as limited to the described order or elements unless stated to that effect. It should be understood that various changes in form and detail may be made without departing from the scope of the appended claims.

---

What is claimed is:

1. A method for treating proliferative diabetic retinopathy (PDR) in a human patient in need thereof, the method comprising:

a) administering to the patient by intravitreal injection three individual 6 mg doses of brolucizumab at 6-week intervals, followed by b) administering to the patient by intravitreal injection additional 6 mg doses of brolucizumab according to a maintenance phase comprising a treatment interval that is once every 12 weeks (q12w).

2. The method of claim 1, further comprising assessing the patient for PDR disease activity before or after administering each maintenance phase dose.

3. The method of claim 2, wherein PDR disease activity is assessed based on identifying best corrected visual acuity (BCVA), ETDRS DRSS score, retinal neovascularization status, and peripheral visual field.

4. The method of claim 2, wherein if worsening of PDR disease activity is identified after a q12w dose, the patient is switched to a q6w dose interval.

5. The method of claim 4, wherein alternatively if disease activity is stable or improved relative to a prior disease activity assessment, the maintenance phase treatment interval is extended by 6 weeks at a time up to a 24 week treatment interval (q24w).

6. The method of claim 4, wherein the worsening of PDR disease activity is new or worsening retinal neovascularization, reperfusion of retinal neovascularization, increase in ETDRS DRSS score, loss in peripheral visual field, and/or developing complications that impact visual acuity compared to any previous assessment.

7. The method of claim 2, wherein at any time during the maintenance phase, the treatment interval is extended to 18 weeks (q18w) or 24 weeks (q24w) if PDR disease activity is stable or improved relative to a prior PDR disease activity assessment.

8. The method of claim 1, wherein the patient does not have macular edema.

9. A method for treating diabetic retinopathy (DR) or proliferative diabetic retinopathy (PDR) comprising administering by intravitreal injection to a human patient in need thereof three individual 6 mg doses of brolucizumab at 6-week intervals in a loading phase, followed by additional 6 mg doses of brolucizumab every 12 weeks (q12w) in a maintenance phase.

10. The method of claim 9, further comprising assessing the patient's DR or PDR disease activity before or after administering each maintenance phase dose.

11. The method of claim 10, wherein DR or PDR disease activity is assessed based on identifying best corrected visual acuity (BCVA), ETDRS DRSS score, retinal neovascularization status, and peripheral visual field.

12. The method of claim 10, wherein at any time during the maintenance phase the dosing intervals are extended to 24 weeks (q24w) if DR or PDR disease activity is improved or stable relative to the prior DR or PDR disease activity assessment.

13. The method of claim 12, wherein if worsening of DR or PDR disease activity is identified after a q12w dose, the patient is switched to a q6w dose interval.

14. The method of claim 13, wherein alternatively if disease activity is stable or improved relative to a prior disease activity assessment, the maintenance phase treatment interval is extended by 6 weeks at a time up to a 24 week treatment interval (q24w).

15. The method of claim 13, wherein the worsening of DR or PDR disease activity is new or worsening retinal neovascularization, reperfusion of retinal neovascularization, increase in ETDRS DRSS score, loss in peripheral visual field, and/or developing complications that impact visual acuity compared to any previous assessment.

16. The method of claim 9, wherein the patient also has does not have macular edema.

17. A method for preventing progression of non-proliferative diabetic retinopathy (NPDR) to proliferative diabetic retinopathy (PDR) in a human patient in need thereof, the method comprising:
a) administering by intravitreal injection to the patient three individual 6 mg doses of brolucizumab at 6-week intervals; followed by
b) administering by intravitreal injection to the patient additional 6 mg doses of brolucizumab according to a maintenance phase comprising a treatment interval that is once every 12 weeks (q12w).

18. The method of claim 17, further comprising assessing the patient for disease activity before or after administering each maintenance dose.

19. The method of claim 18, wherein disease activity is assessed based on identifying best corrected visual acuity (BCVA), ETDRS DRSS score, retinal neovascularization status, and peripheral visual field.

20. The method of claim 18, wherein if worsening of disease activity is identified after a q12w dose, the patient is switched to a q6w dose interval.

21. The method of claim 20, wherein alternatively if disease activity is stable or improved relative to a prior disease activity assessment, the maintenance phase treatment interval is extended by 6 weeks at a time up to a 24 week treatment interval (q24w).

22. The method of claim 20, wherein the worsening of disease activity is new or worsening retinal neovascularization, reperfusion of retinal neovascularization, increase in ETDRS DRSS score (such as an increase of 2 or more steps), loss in peripheral visual field, and/or developing complications that impact visual acuity compared to any previous assessment.

23. The method of claim 18, wherein if disease activity is stable or improved relative to a prior disease activity assessment, the maintenance phase treatment interval is extended by 6 weeks at a time up to a 24 week treatment interval (q24w).

24. The method of claim 17, wherein the patient does not have macular edema.

* * * * *